United States Patent [19]

Muller et al.

[11] Patent Number: 5,380,863
[45] Date of Patent: Jan. 10, 1995

[54] HERBICIDAL SULPHONYLAMINOCARBONYL-TRIAZOLINONES HAVING SUBSTITUENTS WHICH ARE BONDED VIA SULPHUR

[75] Inventors: Klaus-Helmut Muller; Peter Babczinski; Hans-Joachim Santel; Robert R. Schmidt, all of Leverkusen, Germany

[73] Assignee: Bayer Aktiengesellschaft, Leverkusen, Germany

[21] Appl. No.: 136,429

[22] Filed: Oct. 13, 1993

Related U.S. Application Data

[62] Division of Ser. No. 870,867, Apr. 20, 1992, Pat. No. 5,276,162, which is a division of Ser. No. 777,824, Oct. 15, 1991, Pat. No. 5,149,356, which is a division of Ser. No. 596,845, Oct. 12, 1990, Pat. No. 5,085,684.

[30] Foreign Application Priority Data

Oct. 12, 1989 [DE] Germany .............. 3934081
Nov. 3, 1989 [DE] Germany .............. 3936622
Nov. 3, 1989 [DE] Germany .............. 3936623

[51] Int. Cl.$^6$ ............................. C07D 249/12
[52] U.S. Cl. ............................. 548/263.6
[58] Field of Search ..................... 548/263.6

[56] References Cited

U.S. PATENT DOCUMENTS

| | | | |
|---|---|---|---|
| 3,862,125 | 1/1975 | Hoffman et al. | 260/308 R |
| 4,098,896 | 7/1978 | Edwards | 424/269 |
| 4,110,332 | 8/1978 | Edwards | 260/299 |
| 4,931,084 | 6/1990 | Findeisen et al. | 71/92 |
| 5,021,080 | 6/1991 | Muller et al. | 71/92 |
| 5,061,311 | 10/1991 | Findeisen et al. | 71/92 |
| 5,085,684 | 2/1992 | Muller et al. | 71/92 |
| 5,149,356 | 9/1992 | Muller et al. | 71/90 |
| 5,166,356 | 11/1992 | Findeisen et al. | 548/263.8 |

FOREIGN PATENT DOCUMENTS

2527676 1/1977 Germany.

OTHER PUBLICATIONS

JP A-52-125,168 an English translation from Rotha Fullford Leopold, 1977, "Triazolines, Process of Making, and Herbicides", pp. 1-14.

(List continued on next page.)

*Primary Examiner*—Patricia L. Morris
*Attorney, Agent, or Firm*—Sprung Horn Kramer & Woods

[57] ABSTRACT

Herbicidal sulphonylaminocarbonyl-triazolinones having substituents which are bonded via sulphur, of the formula $$R^3-SO_2-NH-CO-N\underset{N}{\overset{\displaystyle\parallel}{\underset{\|}{\diagup}}}\kern-1em\diagdown_{S(O)_n-R^2}^{N-R^1} \quad (I)$$

in which
n represents the numbers 0, 1 or 2,
$R^1$ represents hydrogen, hydroxyl or amino, or represents an optionally substituted radical from the series comprising alkyl, alkenyl, alkinyl, cycloalkyl, aralkyl, aryl, alkoxy, alkenyloxy, alkylamino, cycloalkylamino and dialkylamino,
$R^2$ represents an optionally substituted radical from the series comprising alkyl, alkenyl, alkinyl, cycloalkyl, cycloalkenyl, aralkyl and aryl, and
$R^3$ represents an optionally substituted radical from the series comprising alkyl, aralkyl, aryl and heteroaryl, as well as salts of compounds of the formula (I).

Also new are the compounds of the following formula:

$$Z-CO-N\underset{N}{\overset{\displaystyle\parallel}{\underset{\|}{\diagup}}}\kern-1em\diagdown_{S(O)_n-R^2}^{N-R^1} \quad (IV)$$

in which
n, $R^1$ and $R^2$ have the abovementioned meanings and
Z represents halogen, alkoxy, aralkoxy or aryloxy.

3 Claims, No Drawings

OTHER PUBLICATIONS

*Agricultural Chemistry*, pp. 4–5, Week Y48, J5 2125-168, "Triazoline derivs. used as herbicides -prepd. by reacting corresp. deriv. with isocyanate or carbamoyl chloride", Nippon Soda KK (1977).

*Chemical Abstracts*, vol. 86, 1977, p. 616, 86:189954d, "Insecticidal, acaricidal, andnematocidal triazolylmethyl thiolo(thiono)phosphates and thiolo(thiono)phosphonates"; Lorenz, Hoffman, Hammann, Behrenz, Homeyer; Bayger AG, Ger. Offen. 2,527,676.

*J. Heterocycl. Chem.*, 15, 1978, pp. 377–384, "Cyclization of 1-Substituted-3-Thiosemicarbazides to Triazole Derivatives Under Alkaline Conditions" Altland and Graham, Eastman Kodak Co.

HERBICIDAL SULPHONYLAMINOCARBONYLTRIAZOLINONES HAVING SUBSTITUENTS WHICH ARE BONDED VIA SULPHUR

This is a division of copending application Ser. No. 07/870,867 filed on Apr. 20, 1992, (now issued to U.S. Pat. No. 5,276,162 on Jan. 4, 1994) which is a division of 07/777,824 filed on Oct. 15, 1991 (now issued to Pat. No. 5,149,356 on Sep. 22, 1992), which is a division of 07/596,845 filed on Oct. 12, 1990 (now issued to Pat. No. 5,085,684 on Feb. 4, 1992).

The invention relates to new sulphonylamino-carbonyltriazolinones having substituents which are bonded via sulphur, to a variety of processes for their preparation, and to their use as herbicides.

It is known that certain substituted aminocarbonylimidazolinones, such as, for example, 1-isobutyl-aminocarbonyl-2-imidazolidinone (isocarbamid), have herbicidal properties (cf. R. Wegler, Chemie der Pflanzenschutz-und und Schädlingsbekämpfungsmittel [Chemistry of Plant Protection Agents and Pesticides], volume 5, p. 219, Springer-Verlag, Berlin-Heidelberg-New York, 1977). However, the action of this compound is not satisfactory in all respects.

The new sulphonylaminocarbonyl-triazolinones having substituents which are bonded via sulphur, of the formula (I)

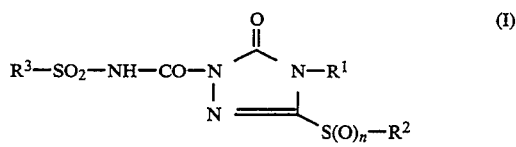

in which
n represents the numbers 0, 1 or 2,
$R^1$ represents hydrogen, hydroxyl or amino, or represents an optionally substituted radical from the series comprising alkyl, alkenyl, alkinyl, cycloalkyl, aralkyl, aryl, alkoxy, alkenyloxy, alkyl-amino, cycloalkylamino and dialkylamino,
$R^2$ represents an optionally substituted radical from the series comprising alkyl, alkenyl, alkinyl, cycloalkyl, cycloalkenyl, aralkyl and aryl, and
$R^3$ represents an optionally substituted radical from the series comprising alkyl, aralkyl, aryl and heteroaryl,
as well as salts of compounds of the formula (I), have now been found.

The new sulphonylaminocarbonyltriazolinones having substituents which are bonded via sulphur, of the general formula (I), are obtained when
a) triazolinones of the general formula (II)

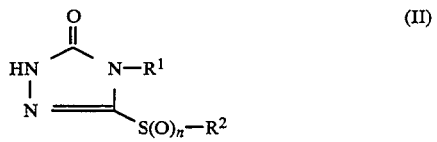

in which
n, $R^1$ and $R^2$ have the abovementioned meanings,
are reacted with sulphonyl isocyanates of the general formula (III)

in which
$R^3$ has the abovementioned meaning, if appropriate in the presence of a diluent, or when
b) triazolinone derivatives of the general formula (IV)

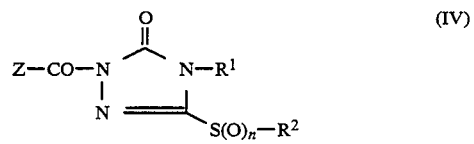

in which
n, $R^1$ and R2 have the abovementioned meanings and Z represents halogen, alkoxy, aralkoxy or aryloxy, are reacted with sulphonamides of the general formula (V)

in which
$R^3$ has the abovementioned meaning, if appropriate in the presence of an acid acceptor and if appropriate in the presence of a diluent, or when
c) triazolinones of the general formula (II)

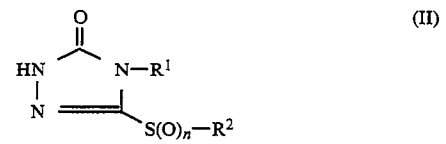

in which
n, $R^1$ and $R^2$ have the abovementioned meanings, are reacted with sulphonamide derivatives of the general formula (VI)

in which
$R^3$ has the abovementioned meaning and
Z represents halogen, alkoxy, aralkoxy or aryloxy, if appropriate in the presence of an acid acceptor and if appropriate in the presence of a diluent, and, if desired, salts are formed by customary methods from the compounds of the formula (I) prepared by process (a), (b) or (c).

The new sulphonylaminocarbonyltriazolinones having substituents which are bonded via sulphur, of the general formula (I), and their salts are distinguished by a powerful herbicidal activity.

Surprisingly, the new compounds of the formula (I) have a considerably better herbicidal action than the herbicide 1-isobutylaminocarbonyl-2-imidazolidinone (isocarbamid), which is known and has a similar structure.

The invention preferably relates to compounds of the formula (I) in which
n represents the numbers 0, 1 or 2,
$R^1$ represents hydrogen, hydroxyl or amino, or represents $C_1$-$C_6$-alkyl which is optionally substituted by fluorine, chlorine, bromine, cyano, $C_1$-$C_4$-alkoxy, $C_1$-$C_4$-alkylcarbonyl or $C_1$-$C_4$-alkoxy-carbonyl, or represents $C_3$-$C_6$-alkenyl or $C_3$-$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxy-carbonyl, or represents $C_1$–$C_6$-alkoxy which is optionally substituted by fluorine, chlorine, cyano, phenyl, $C_1$–$C_4$-alkoxy or $C_1$–$C_4$-alkoxy-carbonyl, or represents $C_3$–$C_4$-alkenyloxy, or represents $C_1$–$C_4$-alkylamino which is optionally substituted by fluorine, cyano, $C_1$–$C_4$-alkoxy or $C_1$–$C_4$-alkoxy-carbonyl, or represents $C_3$–$C_6$-cycloalkylamino or di-($C_1$–$C_4$-alkyl)-amino, $R^2$ represents $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxycarbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkyl-sulphonyl and/or $C_1$–$C_4$-alkoxy-carbonyl, and $R^3$ represents the group

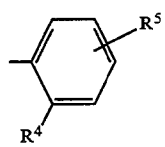

where $R^4$ and $R^5$ are identical or different and represent hydrogen, fluorine, chlorine, bromine, iodine, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylamino-carbonyl, di($C_1$–$C_4$-alkyl)amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkyl-sulphonyl, di-($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxy-carbonyl, carboxyl or phenyl), or represent $C_2$–$C_6$-alkinyl (which is optionally substituted by fluorine, chlorine, bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkyl-sulphonyl), or represent $C_1$–$C_4$-alkylthio (which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or represent $C_3$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy or $C_3$–$C_6$-alkinylthio, or represent the radical —S(O)-$p$—$R^6$ where p represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino or phenyl, or represents the radical —NHOR$^7$ where $R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxycarbonyl, $C_1$–$C_4$-alkyl-amino-carbonyl or di-($C_1$–$C_4$-alkyl)-amino-carbonyl), or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or represents benzhydryl, or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl), $R^4$ and/or $R^5$ furthermore represent phenyl or phenoxy, or represent $C_1$–$C_4$-alkylcarbonylamino, $C_1$–$C_4$-alkoxycarbonylamino, $C_1$–$C_4$-alkylaminocarbonyl-amino or di-($C_1$–$C_4$-alkyl)-amino-carbonylamino, or represent the radical -CO-$R^8$ where $R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkoxyamino, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (each of which is optionally substituted by fluorine and/or chlorine), $R^4$ and/or $R^5$ furthermore represent trimethylsilyl, thiazolinyl, $C_1$–$C_4$-alkylsulphonyloxy or di-($C_1$–$C_4$-alkyl)-aminosulphonylamino, or represent the radical —CH=N—$R^9$ where $R^9$ represents $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, or represents benzyl which is optionally substituted by fluorine or chlorine, or represents $C_3$–$C_6$-alkenyl or $C_3$–$C_6$-alkinyl, each of which is optionally substituted by fluorine or chlorine, or represents phenyl which is optionally substituted by fluorine, chlorine, bromine, $C_1$-$C_4$-alkyl, $C_1$-$C_4$-alkoxy, trifluoro-methyl, trifluoromethoxy or trifluoromethylthio, or represents $C_1$-$C_6$-alkoxy, $C_3$-$C_6$-alkenoxy, $C_3$-$C_6$-alkinoxy or benzyloxy, each of which is optionally substituted by fluorine and/or chlorine, or represents amine, $C_1$-$C_4$-alkylamino, di-($C_1$-$C_4$-alkyl)-amino, phenylamino, $C_1$-$C_4$-alkyl-carbonyl-amino, $C_1$-$C_4$-alkoxy-carbonylamino or $C_1$-$C_4$-alkyl-sulphonylamino, or represents phenylsulphonylamino which is optionally substituted by fluorine, chlorine, bromine or methyl, furthermore $R^3$ represents the radical

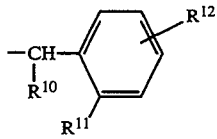

where $R^{10}$ represents hydrogen or $C_1$-$C_4$-alkyl, $R^{11}$ and $R^{12}$ are identical or different and represent hydrogen, fluorine, chlorine, bromine, nitro, cyano, $C_1$-$C_4$-alkyl (which is optionally substituted by fluorine and/or chlorine), $C_1$-$C_4$-alkoxy (which is optionally substituted by fluorine and/or chlorine), carboxyl, $C_1$-$C_4$-alkoxy-carbonyl, dimethylaminocarbonyl, $C_1$-$C_4$-alkyl-sulphonyl or di-($C_1$-$C_4$-alkyl)-aminosulphonyl; furthermore $R^3$ represents the radical

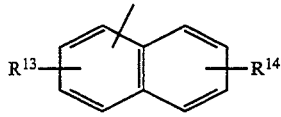

where $R^{13}$ and $R^{14}$ are identical or different and represent hydrogen, fluorine, chlorine, bromine, nitro, cyano, $C_1$-$C_4$-alkyl (which is optionally substituted by fluorine and/or chlorine) or $C_1$-$C_4$-alkoxy (which is optionally substituted by fluorine and/or chlorine);

furthermore $R^3$ represents the radical

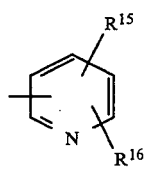

where $R^{15}$ and $R^{16}$ are identical or different and represent hydrogen, fluorine, chlorine, bromine, nitro, cyano, $C_1$-$C_4$-alkyl (which is optionally substituted by fluorine and/or chlorine), $C_1$-$C_4$-alkoxy (which is optionally substituted by fluorine and/or chlorine), or represents $C_1$-$C_4$alkylthio, $C_1$-$C_4$-alkyl-sulphinyl or $C_1$-$C_4$-alkyl-sulphonyl (each of which is optionally substituted by fluorine and/or chlorine), or represents aminosulphonyl, mono-($C_1$-$C_4$-alkyl)-aminosulphonyl, or represents di-($C_1$-$C_4$-alkyl)-aminosulphonyl or $C_1$-$C_4$-alkoxycarbonyl or dimethylaminocarbonyl;

furthermore $R^3$ represents the radical

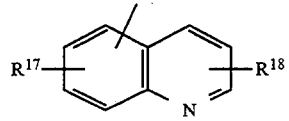

where $R^{17}$ and $R^{18}$ are identical or different and represent hydrogen, fluorine, chlorine, bromine, $C_1$-$C_4$-alkyl (which is optionally substituted by fluorine and/or bromine), $C_1$-$C_4$-alkoxy (which is optionally substituted by fluorine and/or chlorine), or represent $C_1$-$C_4$-alkylthio, $C_1$-$C_4$-alkylsulphinyl or $C_1$-$C_4$-alkyl-sulphonyl (which is optionally substituted by fluorine and/or chlorine), or represent di-($C_1$-$C_4$-alkyl)-aminosulphonyl;

furthermore $R^3$ represents the radical

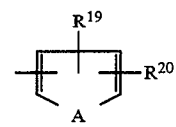

where $R^{19}$ and $R^{20}$ are identical or different and represent hydrogen, fluorine, chlorine, bromine, cyano, nitro, $C_1$-$C_4$-alkyl (which is optionally substituted by fluorine and/or chlorine), $C_1$-$C_4$-alkoxy (which is optionally substituted by fluorine and/or chlorine), $C_1$-$C_4$-alkylthio, $C_1$-$C_4$-alkylsulphinyl or $C_1$-$C_4$-alkylsulphonyl (which is optionally substituted by fluorine and/or chlorine), di-($C_1$-$C_4$-alkyl)-aminosulphonyl, $C_1$-$C_4$-alkoxy-carbonyl or dimethylaminocarbonyl, and A represents oxygen, sulphur or the group N-$Z^1$ where $Z^1$ represents hydrogen, $C_1$-$C_4$-alkyl (which is optionally substituted by fluorine, chlorine, bromine or cyano), $C_3$-$C_6$-cycloalkyl, benzyl, phenyl (which is optionally substituted by fluorine, chlorine, bromine or nitro), $C_1$-$C_4$alkylcarbonyl, $C_1$-$C_4$-alkoxy-carbonyl or di-($C_1$-$C_4$-alkyl)-aminocarbonyl;

furthermore $R^3$ represents the radical

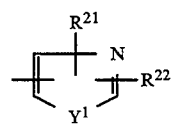

where $R^{21}$ and $R^{22}$ are identical or different and represent hydrogen, $C_1$-$C_4$-alkyl, halogen, $C_1$-$C_4$-alkoxycarbonyl, $C_1$-$C_4$-alkoxy or $C_1$-$C_4$-halogenoalkoxy, $Y^1$ represents sulphur or the group N-$R^{23}$ where $R^{23}$ represents hydrogen or $C_1$-$C_4$-alkyl;

furthermore $R^3$ represents the radical

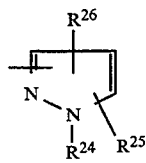

where
R³ represents hydrogen, $C_1-C_4$-alkyl, benzyl, pyridyl, quinolinyl or phenyl, R²⁵ represents hydrogen, halogen, cyano, nitro, $C_1-C_4$-alkyl (which is optionally substituted by fluorine and/or chlorine), $C_1-C_4$-alkoxy (which is optionally substituted by fluorine and/or chlorine), dioxolanyl or $C_1-C_4$-alkoxy-carbonyl and R²⁶ represents hydrogen, halogen or $C_1-C_4$-alkyl; furthermore R³ represents one of the groups listed below,

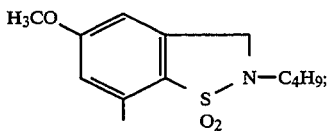

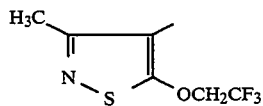

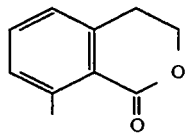

The invention furthermore preferably relates to sodium salts, potassium salts, magnesium salts, calcium salts, ammonium salts, $C_1-C_4$-alkyl-ammonium salts, di-($C_1-C_4$-alkyl)-ammonium salts, tri-($C_1-C_4$-alkyl)-ammonium salts, $C_5$- or $C_6$-cycloalkyl-ammonium salts and di-($C_1-C_2$-alkyl)-benzyl-ammonium salts of compounds of the formula (I) in which n, $R^1$, $R^2$ and $R^3$ have the meanings indicated above as being preferred.

In particular, the invention relates to compounds of the formula (I) in which n represents the numbers 0, 1 or 2, R¹ represents hydrogen or amino, or represents $C_1-C_4$-alkyl which is optionally substituted by fluorine, cyano, methoxy or ethoxy, or represents allyl, or represents $C_3-C_6$-cycloalkyl, or represents benzyl, or represents phenyl, or represents $C_1-C_4$-alkoxy, or represents $C_3-C_4$-alkenyloxy, or represents $C_1-C_3$-alkylamino, $C_3-C_6$-cycloalkylamino, or represents di-($C_1-C_3$-alkyl)-amino, R² represents hydrogen, or represents $C_1-C_4$-alkyl which is optionally substituted by fluorine and/or chlorine, methoxy or ethoxy, or represents $C_3-C_6$-alkenyl which is optionally substituted by fluorine and/or chlorine, or represents $C_3-C_6$-cycloalkyl, or represents benzyl which is optionally substituted by fluorine, chlorine and/or methyl, and represents the group

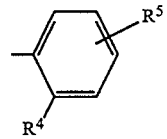

where
R⁴ represents fluorine, chlorine, bromine, methyl, trifluoromethyl, methoxy, difluoromethoxy, trifluoromethoxy, 2-chloro-ethoxy, 2-methoxy-ethoxy, $C_1-C_3$-alkylthio, $C_1-C_3$-alkylsulphinyl, $C_1-C_3$-alkylsulphonyl, dimethylaminosulphonyl, diethylaminosulphonyl, N-methoxy-N-methylamino-sulphonyl, methoxyaminosulphonyl, phenyl, phenoxy or $C_1-C_3$-alkoxy-carbonyl, and R⁵ represents hydrogen, fluorine, chlorine or bromine;
furthermore
represents the radical

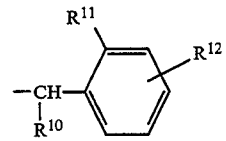

where
R¹⁰ represents hydrogen,
R¹¹ represents fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl, and
R¹² represents hydrogen;
furthermore
R³ represents the radical

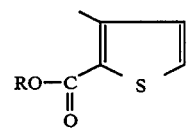

where R represents $C_1-C_4$-alkyl, or represents the radical

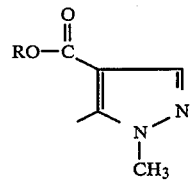

where R represents $C_1-C_4$-alkyl.

Examples of the compounds according to the invention are listed in Table 1 below—cf. also the Preparation Examples.

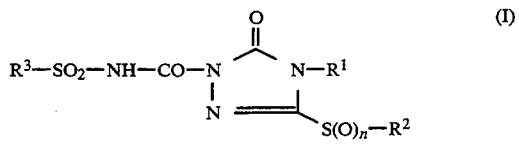

TABLE 1
Examples of the compounds of the formula (I)
| R¹ | R² | R³ | n |
|---|---|---|---|
|  | CH₃ | 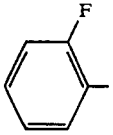 | 0 |
|  | CH₃ | 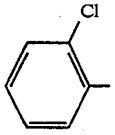 | 0 |
| CH₃ | C₂H₅ | 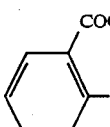 | 0 |
| CH₃ | CH₂—CH=CH₂ | 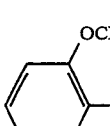 | 0 |
| CH₃ | CH₃ | 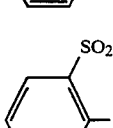 | 0 |
| CH₃ | CH₃ | 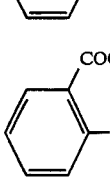 | 0 |
| CH₃ | C₂H₅ | 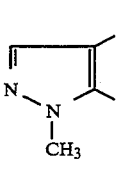 | 0 |
| CH₃ | C₂H₅ | 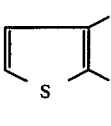 | 0 |
| CH₃ | C₂H₅ | 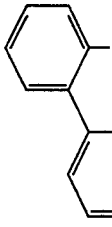 | 0 |
| C₂H₅ | C₂H₅ | 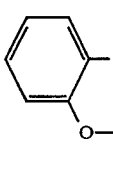 | 0 |

TABLE 1-continued
Examples of the compounds of the formula (I)
| R¹ | R² | R³ | n |
|---|---|---|---|
| $C_2H_5$ | $C_3H_7$ | 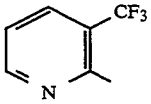 | 0 |
|  | $CH_3$ | 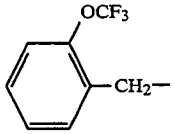 | 0 |
|  | $C_2H_5$ | 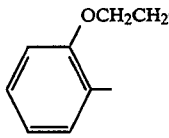 | 0 |
|  | $CH(CH_3)_2$ | 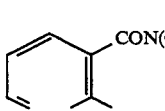 | 0 |
| $CH_3$ | $CH(CH_3)_2$ | 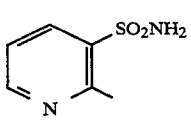 | 0 |
| $CH_3$ | $CH_2-CH=CH_2$ | 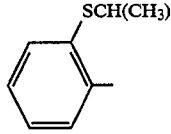 | 1 |
| $C_2H_5$ | $CH_3$ | 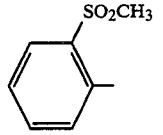 | 2 |
| $C_2H_5$ | $C_2H_5$ | 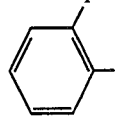 | 0 |
| $CH_3$ | $C_2H_5$ | 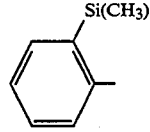 | 0 |
| $C_2H_5$ | $C_3H_7$ | 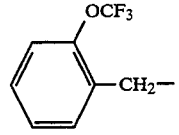 | 0 |
| $CH_3$ | $C_2H_5$ | 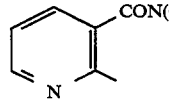 | 0 |

TABLE 1-continued

Examples of the compounds of the formula (I)

| R¹ | R² | R³ | n |
|---|---|---|---|
| CH₂-phenyl | CH₃ | 2-Br-phenyl | 0 |
| cyclopropyl | C₂H₅ | 2-(OCH₂CH₂—OCH₃)-phenyl | 0 |
| cyclobutyl | CH₃ | 4-Br-5-methyl-1-methyl-pyrazol-3-yl | 0 |
| cyclopentyl | C₂H₅ | 2-SO₂N(CH₃)₂-phenyl | 0 |
| cyclohexyl-H | C₃H₇-n | 2-(OCHF₂)-benzyl (—CH₂—) | 0 |
| CH₃ | C₂H₅ | 2-COOCH(CH₃)₂-4-Cl-phenyl | 0 |
| CH₃ | CH₃ | 2-COOC₂H₅-4-(F₂CHO)-phenyl | 0 |
| CH₃ | C₂H₅ | 2-phenoxy-phenyl | 0 |
| CH₃ | —CH₂—C≡CH | 2-(thiazol-2-yl)-phenyl | 0 |

TABLE 1-continued

Examples of the compounds of the formula (I)

| R¹ | R² | R³ | n |
|---|---|---|---|
| CH₃ | C₂H₅ | 2-(2,2,2-trifluoroethoxy)phenyl (O—CH₂—CF₃ on phenyl) | 0 |
| cyclopropyl | C₂H₅ | methyl 5-methyl-1-phenyl-1H-pyrazole-4-carboxylate-3-yl (COOCH₃, pyrazole with N–N–phenyl) | 0 |
| cyclopropyl | CH₃ | methyl 5-methyl-1-(isoquinolin-1-yl)-1H-pyrazole-4-carboxylate-3-yl (COOCH₃, pyrazole N-linked to isoquinoline) | 0 |
| CH₃ | CH₃ | 4-chloro-5-methylisothiazol-3-yl (Cl on isothiazole, N–S) | 0 |
| CH₃ | C₃H₇ | 5-(N,N-dimethylcarbamoyl)-2,6-dimethylpyridin-3-yl (CON(CH₃)₂, H₃C–pyridine–CH₃) | 0 |
| C₂H₅ | C₂H₅ | methyl 3-methylthiophene-2-carboxylate (COOCH₃ on thiophene) | 0 |
| CH₂—CH=CH₂ | C₂H₅ | 2-(methoxycarbonyl)benzyl (COOCH₃, —CH₂— on phenyl) | 0 |
| CH₂—CH=CH₂ | CH₃ | 4-bromo-5-methyl-1-methyl-1H-pyrazol-3-yl (Br, N–N–CH₃) | 0 |
| OCH₃ | CH₃ | 2-(methoxycarbonyl)phenyl (COOCH₃ on phenyl) | 0 |
| OC₂H₅ | C₂H₅ | 2-[N-methyl-N-methoxysulfamoyl]phenyl (SO₂NCH₃(OCH₃) on phenyl) | 0 |

TABLE 1-continued

Examples of the compounds of the formula (I)

| R¹ | R² | R³ | n |
|---|---|---|---|
| OC$_3$H$_7$ | CH$_2$—CH=CH$_2$ | 2-methylphenyl | 0 |
| CH$_3$ | CH$_3$ | 2-methoxyphenyl | 0 |
| cyclopropyl | C$_2$H$_5$ | 2-chloro-6-methylphenyl | 2 |
| cyclopropyl | C$_2$H$_5$ | 2-bromo-6-methylphenyl | 0 |
| C$_2$H$_5$ | C$_2$H$_5$ | 4-chloro-5-methyl-1-methyl-1H-pyrazol-3-yl | 0 |
| CH$_3$ | C$_2$H$_5$ | 2-(phenylsulfonyl)phenyl | 0 |
| CH$_3$ | C$_3$H$_7$ | 2-(difluoromethoxy)benzyl | 0 |
| OCH$_3$ | CH$_3$ | 3-methyl-2-(methoxycarbonyl)thiophen-2-yl | 0 |
| OC$_2$H$_5$ | CH$_3$ | 2-methoxyphenyl | 0 |
| OC$_2$H$_5$ | C$_2$H$_5$ | 2-(2-chloroethoxy)phenyl | 0 |

TABLE 1-continued

Examples of the compounds of the formula (I)

| $R^1$ | $R^2$ | $R^3$ | n |
|---|---|---|---|
| O—CH₂—CH=CH₂ | C₂H₅ | 2-F-phenyl | 0 |
| CH₃ | C₂H₅ | 2-(isoxazolin-2-yl)-phenyl | 0 |
| CH₃ | CH₃ | 3-CF₃-pyridin-2-yl | 0 |
| N(CH₃)₂ | CH₃ | naphthyl | 0 |
| CH₃ | C₂H₅ | 3-SO₂NH₂-pyridin-2-yl | 0 |
| OCH₃ | C₂H₅ | 3-SO₂NH₂-pyridin-2-yl | 0 |
| cyclopropyl | CH₃ | 3-SO₂NH₂-pyridin-2-yl | 0 |
| CH₃ | C₂H₅ | 3-methyl-2-(OCF₂CF₂Cl)-thien-yl | 0 |
| N(CH₃)₂ | CH₃ | 2-(OCH₂CH₂Cl)-phenyl | 0 |

If, for example, 2,6-difluoro-phenyl isocyanate and 5-ethylthio-4-methoxy-2,4-dihydro-3H-1,2,4-triazol-3-one are used as starting substances, the course of the reaction in process (a) according to the invention can be outlined by the following equation:

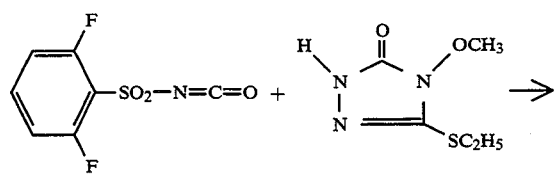

-continued

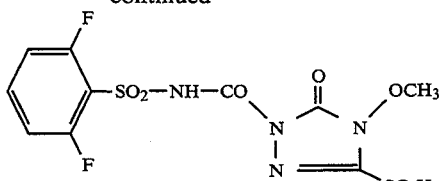

If, for example, 2-methylthio-benzenesulphonamide and 2-chlorocarbonyl-4-dimethylamino-5-propylthio-2,4-dihydro-3H-1,2,4-triazol-3-one are used as starting substances, the course of the reaction in process (b)

according to the invention can be outlined by the following equation:

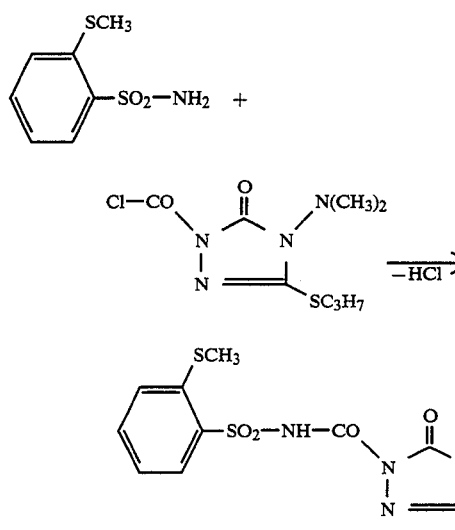

If, for example, N-methoxycarbonyl-2-methoxy-benzenesulphonamide and 5-methylsulphonyl-4-difluoromethyl-2,4-dihydro-3H-1,2,4-triazol-3-one are used as starting substances, the course of the reaction in process (c) according to the invention can be outlined by the following equation:

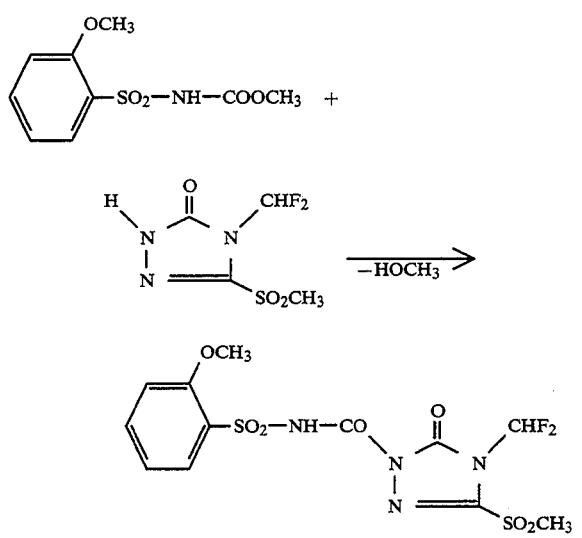

Formula (II) provides a general definition of the triazolinones to be used as starting substances in processes (a) and (c) according to the invention for the preparation of compounds of the formula (I).

In Formula (II), n, $R^1$ and $R^2$ preferably, or in particular, have those meanings which have already been mentioned above in connection with the description of the compounds of the formula (I) according to the invention as being preferred, or particularly preferred, for n, $R^1$ and $R^2$.

Examples of the starting substances of the formula (II) are listed in Table 2 below.

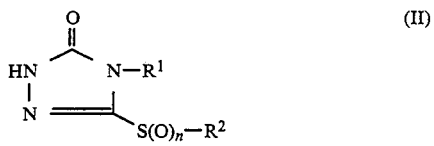

TABLE 2

| Examples of the starting substances of the formula (II) | | |
|---|---|---|
| $R^1$ | $R^2$ | n |
| H | $CH_3$ | 0 |
| $CH_3$ | $CH_3$ | 0 |
| $C_2H_5$ | $CH_3$ | 0 |
| $C_3H_7$ | $CH_3$ | 0 |
| $CH(CH_3)_2$ | $CH_3$ | 0 |
| $C_4H_9$ | $CH_3$ | 0 |
| cyclopropyl | $CH_3$ | 0 |
| $CH_3$ | $C_2H_5$ | 0 |
| $CH_3$ | $C_3H_7$ | 0 |
| $CH_3$ | $CH(CH_3)_2$ | 0 |
| $CH_3$ | $CH_2-CH=CH_2$ | 0 |
| $CH_3$ | $CH_2$-phenyl | 0 |
| $CH_3$ | $CH_2-C{\equiv}CH$ | 0 |
| $C_2H_5$ | $C_2H_5$ | 0 |
| $C_3H_7$ | $C_2H_5$ | 0 |
| cyclopropyl | $C_2H_5$ | 0 |
| $CH_2-CH=CH_2$ | $C_2H_5$ | 0 |
| $CH_2-CHBr-CH_2Br$ | $C_2H_5$ | 0 |
| cyclopropyl | $C_3H_7$ | 0 |
| cyclopropyl | $CH_2-CH=CH_2$ | 0 |
| cyclopropyl | $CH(CH_3)_2$ | 0 |
| $C_2H_5$ | $CH(CH_3)_2$ | 0 |
| $C_3H_7$ | $CH(CH_3)_2$ | 0 |
| $CH_2-CH=CH_2$ | $C_3H_7$ | 0 |
| $C_2H_5$ | $C_3H_7$ | 0 |
| $C_2H_5$ | $-CH_2-C{\equiv}CH$ | 0 |
| $C_3H_7$ | $C_3H_7$ | 0 |
| $OCH_3$ | $CH_3$ | 0 |
| $OCH_3$ | $C_2H_5$ | 0 |

The starting substances of the formula (II) are known and/or can be prepared by processes known per se (cf. J. Heterocycl. Chem. 15 (1978), pp. 377–384; DE-OS (German Published Specification) 2,250,572; DE-OS (German Published Specification) 2,527,676; DE-OS (German Published Specification) 3,709,574; U.S. Pat. No. 4,098,896; U.S. Pat. No. 4,110 332; JP-A-52-125 168).

Formula (III) provides a general definition of the sulphonyl isocyanates also to be used as starting substances in process (a) according to the invention for the preparation of compounds of the formula (I).

In formula (III), $R^3$ preferably, or in particular, has the meaning which has already been mentioned above in connection with the description of the compounds of the formula (I) according to the invention as being preferred, or particularly preferred, for $R^3$.

Examples of the starting substances of the formula (III) which may be mentioned are: 2-fluoro-, 2-chloro-, 2-bromo-, 2-methyl-, 2-methoxy-, 2-trifluoromethyl-, 2-difluoromethoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-phenylsulphonyl isocyanate, 2-fluoro-, 2-chloro-, 2-difluoromethoxy-, 2-trifluoromethoxy-, 2-methoxycarbonyl- and 2-ethoxycarbonyl-benzylsulphonyl isocyanate, 2-methoxycarbonyl-3-thienylsulphonyl isocyanate, 4-methoxycarbonyl- and 4-ethoxycarbonyl-1-methyl-pyrazol-5-yl-sulphonylisocyanate.

The sulphonyl isocyanates of the formula (III) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (a) according to the invention for the preparation of the new compounds of the formula (I) is preferably carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

In process (a) according to the invention, the reaction temperatures can be varied within a substantial range. In general, the process is carried out at temperatures between 0° C. and 150° C., preferably at temperatures between 10° C. and 80° C.

Process (a) according to the invention is generally carried out under atmospheric pressure.

For carrying out process (a) according to the invention, between 1 and 3 moles, preferably between 1 and 2 moles, of sulphonyl isocyanate of the formula (III) are generally employed per mole of triazolinone of the formula (II).

The reactants can be combined in any desired sequence. The reaction mixture is stirred until the reaction is complete, and the product is isolated by filtration with suction. In another work-up variant, the mixture is concentrated, and the crude product which remains in the residue is crystallized with a suitable solvent, such as, for example, diethyl ether. The product of the formula (I), which in this process is obtained in crystalline form, is isolated by filtration with suction.

Formula (IV) provides a general definition of the triazolinone derivatives to be used as starting substances in process (b) according to the invention for the preparation of compounds of the formula (I).

In formula (IV), n, $R^1$ and $R^2$ preferably, or in particular, have those meanings which have already been mentioned above in connection with the description of the compounds of the formula (I) according to the invention as being preferred, or particularly preferred, for n, $R^1$ and $R^2$, and z preferably represents chlorine, $C_1$–$C_4$-alkoxy, benzyloxy or phenoxy, in particular methoxy or phenoxy.

Possible examples of the starting substances of formula (IV) are the compounds of the formula (IV) to be prepared from the compounds of the formula (II) listed in Table 2 and phosgene, methyl chloroformate, benzyl chloroformate, phenyl chloroformate or diphenyl carbonate.

The starting substances of the formula (IV) were hitherto unknown.

The new triazolinone derivatives of the formula (IV) are obtained when triazolinones of the general formula (II)

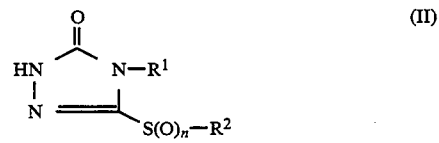

in which n, $R^1$ and $R^2$ have the abovementioned meanings, are reacted with carbonic acid derivatives of the general formula (XI)

in which

Z has the abovementioned meaning and $Z^1$ represents a leaving group, such as chlorine, methoxy, benzyloxy or phenoxy, if appropriate in the presence of a diluent, such as, for example, tetrahydrofuran, and if appropriate in the presence of an acid acceptor, such as, for example, sodium hydride or potassium tert-butylate, at temperatures between −20° C. and +100° C. (cf. also the Preparation Examples).

Formula (V) provides a general definition of the sulphonamides also to be used as starting substances in process (b) according to the invention for the preparation of compounds of the formula (I).

In formula (V), $R^3$ preferably, or in particular, has the meaning which has already been mentioned above in connection with the description of the compounds of the formula (I) according to the invention as being preferred, or particularly preferred, for $R^3$.

Examples of the starting substances of the formula (V) which may be mentioned are: 2-fluoro-, 2-chloro-, 2-bromo-, 2-methyl-, 2-methoxy-, 2-trifluoromethyl-, 2-difluoromethoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-benzenesulphonamide, 2-fluoro-, 2-chloro-, 2-difluoromethoxy-, 2-trifluoromethoxy-, 2-methoxycarbonyl- and 2-ethoxycarbonyl-phenylmethanesulphonamide, 2-methoxycarbonyl-3-thiophenesulphonamide, 4-methoxycarbonyl- and 4-ethoxycarbonyl-1-methyl-pyrazol-5-sulphonamide.

The sulphonamides of the formula (V) are known and/or can be prepared by processes known per se (cf. U.S. Pat. Nos. 4,127,405, 4,169,179, 4,371,391; EP-A 7,687, 13,480, 21,641, 23,141, 23,422, 30,139, 35,893, 44,808, 44,809, 48,143, 51,466, 64,322, 70,041, 173,312).

In process (b) according to the invention, preparation of the new compounds of the formula (I) is preferably carried out using diluents. Diluents which are suitable for this purpose are virtually all inert organic solvents, for example those which have been indicated above for process (a) according to the invention.

Acid acceptors which can be employed in process (b) according to the invention are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo[2,2,2]-octane (DABCO).

In process (b) according to the invention, the reaction temperatures can be varied within a substantial range. In general, the process is carried out at temperatures between 0° C. and 100° C., preferably at temperatures between 10° C. and 60° C.

In general, process (b) according to the invention is carried out under atmospheric pressure. However, it is also possible to carry out the process under increased or reduced pressure.

For carrying out process (b) according to the invention, the specifically required starting substances are generally employed in approximately equimolar amounts. However, it is also possible to use one of the two components employed in each case in a substantial excess. In general, the reactions are carried out in a suitable diluent in the presence of an acid acceptor, and the reaction mixture is stirred for several hours at the specifically required temperature. In process (b) according to the invention, working-up is carried out in each case by customary methods.

The triazolinones of the formula (II) to be used as starting substances in process (c) according to the invention for the preparation of compounds of the formula (I) have already been described as starting substances for process (a) according to the invention.

Formula (VI) provides a general definition of the sulphonamide derivatives also to be used as starting substances in process (c) according to the invention for the preparation of compounds of the formula (I).

In formula (VI), $R^3$ and Z preferably, or in particular, have those meanings which have already been mentioned above in connection with the description of the compounds of the formula (I), or (IV), according to the invention as being preferred, or particularly preferred, for $R^3$ and Z.

Process (c) according to the invention is preferably carried out using diluents. The same organic solvents which have been mentioned above in connection with the description of process (a) according to the invention are suitable for this purpose.

If appropriate, process (c) is carried out in the presence of an acid acceptor. The same acid-binding agents which have been mentioned above in connection with the description of process (b) according to the invention are suitable for this purpose.

In process (c) according to the invention, the reaction temperatures can be varied within a substantial range. In general, the process is carried out at temperatures between 0° C. and 100° C., preferably at temperatures between 10° C. and 60° C.

In general, process (c) according to the invention is carried out under atmospheric pressure. However, it is also possible to carry out the process under increased or reduced pressure.

For carrying out process (c) according to the invention, the specifically required starting substances are generally employed in approximately equimolar amounts. However, it is also possible to use one of the two specifically employed components in a substantial excess. In general, the reactions are carried out in a suitable diluent in the presence of an acid acceptor, and the reaction mixture is stirred for several hours at the specifically required temperature. In process (c) according to the invention, working-up is carried out in each case by customary methods.

For converting the compounds of the formula (I) into salts, they are stirred with suitable salt formers, such as, for example, sodium hydroxide, sodium methylate, sodium ethylate, potassium hydroxide, potassium methylate or potassium ethylate, ammonia, isopropylamine, dibutylamine or triethylamine, in suitable diluents, such as, for example, water, methanol or ethanol. The salts can be isolated as crystalline products - then if appropriate after concentration.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop-fields, on lawn, turf and pasture-land, and for the selective combating of weeds in annual cultures.

In particular, the compounds of the formula (I) according to the invention are suitable for selectively combating monocotyledon and dicotyledon weeds in monocotyledon crops, either using the pre-emergence or the post-emergence method. They are markedly more effective than, for example, isocarbamid.

To a certain extent, the compounds according to the invention also show fungicidal action, for example against Pyricularia on rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3(2,2-dimethylpropyl)-1,3,5-triazine-2,4-(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans; furthermore also 2,4-dichlrophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N{[(4-methoxy-6-methyl-1,3,5-triazin-2-yl)-amino]-carbonyl}benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN);2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridin-yl)-oxy]-acetic acid or its 1-methylheptyl ester (FLUROXYPYR); N-phosphonomethylglycin (GLYPHOSATE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N'-methyl-2-

(1,3-benzothiazol-2-yloxy)-acetanilide (MEFENACET); 2-{[[((4-methoxy-6-methyl-1,3,5-triazin-2-yl)amino)-carbonyl]-amino]-sulphonyl}-benzoic acid or its methyl ester (METSULFURON); N-(1-ethyl-propyl)-3,4-dimethyl-2,6-dinitroaniline (PENDIMETHALIN); 0-(6-chloro-3-phenyl-pyridazin-4-yl)-S-octyl thiocarbamate (PYRIDATE); 4-ethylamino-2-t-butylamino-6-methylthio-s-triazine (TERBUTRYNE) and methyl 3-[[[[(4-methoxy-6-methyl-1,3,5-triazin-2-yl)-amino]-carbonyl]-amino]sulphonyl]-thiophene-2-carboxylate (THIAMETURON). Surprisingly, some mixtures also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

Example 1

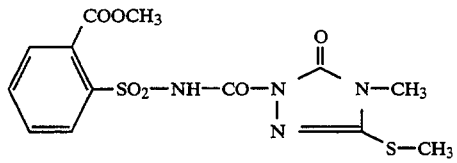

(Process (a))

3.0 g (20.7 mmol) of 4-methyl-5-methylthio-2,4-dihydro-3H-1,2,4-triazol-3-one are dissolved in 60 ml of acetonitrile, and 7.0 g (29 mmol) of 2-methoxycarbonyl-phenylsulphonyl-isocyanate, dissolved in 20 ml of acetonitrile, are added to this solution with stirring. The reaction mixture is stirred at 20° C. for 6 hours. The product which is obtained in crystalline form is then isolated by filtration with suction.

This gives 6.0 g (75% of theory) of 4-methyl-5-methylthio-2-(2-methoxycarbonyl-phenylsulphonyl-aminocarbonyl)-2,4-dihydro-3H-1,2,4-triazol-3-one of melting point 184° C.

Example 2

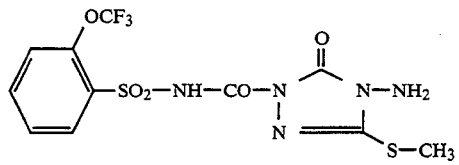

(Process (b))

1.7 g (11.2 mmol) of 1,8-diazabicyclo-[5,4,0]-undec-7-ene (DBU) and 2.7 g (11.2 mmol.) of 2-trifluoromethoxybenzenesulphonamide are added to a solution of 3.0 g (11.3 mmol) of 4-amino-5-methylthio-2-phenoxycarbonyl-2,4-dihydro-3H-1,2,4-triazol-3-one in 60 ml of methylene chloride. The reaction mixture is stirred for 4 hours at 20° C., then washed twice with 1% strength hydrochloric acid and three times with water, dried with sodium sulphate, and filtered. The filtrate is concentrated, the residue is stirred with diethyl ether, and the product which is obtained in crystalline form is isolated by filtration with suction.

This gives 2.1 g (45% of theory) of 4-amino-5-methylthio-2-(2-trifluoromethoxy-phenylsulphonyl-aminocarbonyl)-2,4-dihydro-3H-1,2,4-triazol-3one of melting point 136° C.

For example, the compounds of the formula (I) listed in Table 3 below can also be prepared analogously to Examples 1 and 2 and following the general description of the preparation processes according to the invention.

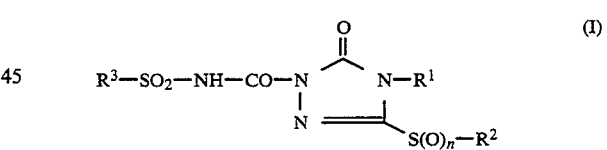

TABLE 3

Preparation Examples of the compounds of the formula (I)

| Ex. No. | R¹ | R² | R³ | n | Melting point (°C.) |
|---|---|---|---|---|---|
| 3 | CH₃ | C₂H₅ | ⟨2-COOCH₃-phenyl⟩ | 0 | 149 |
| 4 | CH₃ | CH(CH₃)₂ | ⟨2-COOCH₃-phenyl⟩ | 0 | 161 |

TABLE 3-continued

Preparation Examples of the compounds of the formula (I)

| Ex. No. | R¹ | R² | R³ | n | Melting point (°C.) |
|---|---|---|---|---|---|
| 5 | $CH_3$ | $CH_2CH=CH_2$ | 2-($COOCH_3$)phenyl | 0 | 140 |
| 6 | $C_2H_5$ | $C_2H_5$ | 2-($COOCH_3$)phenyl | 0 | 128 |
| 7 | $C_2H_5$ | $CH_3$ | 2-($COOCH_3$)phenyl | 0 | 167 |
| 8 | $C_2H_5$ | $CH_2C_6H_5$ | 2-($COOCH_3$)phenyl | 0 | 185 |
| 9 | $CH_3$ | $CH_2C_6H_5$ | 2-($COOCH_3$)phenyl | 0 | 143 |
| 10 | $CH_2C_6H_5$ | $CH_3$ | 2-($COOCH_3$)phenyl | 0 | 134 |
| 11 | $CH(CH_3)_2$ | $CH_3$ | 2-($COOCH_3$)phenyl | 0 | 142 |
| 12 | 3-Cl-phenyl | $CH_3$ | 2-($COOCH_3$)phenyl | 0 | 205 |
| 13 | $CH_3$ | $C_3H_7$ | 2-($COOCH_3$)phenyl | 0 | 142 |
| 14 | $C_2H_5$ | $-CH_2CH=CH_2$ | 2-($COOCH_3$)phenyl | 0 | 111 |

TABLE 3-continued
Preparation Examples of the compounds of the formula (I)
| Ex. No. | R¹ | R² | R³ | n | Melting point (°C.) |
|---|---|---|---|---|---|
| 15 | C₂H₅ | C₃H₇ | 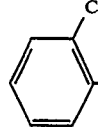 | 0 | 125 |
| 16 | C₂H₅ | CH(CH₃)₂ | 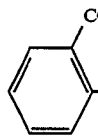 | 0 | 131 |
| 17 | CH₃ | CH₃ | 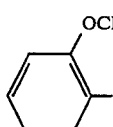 | 0 | 150 |
| 18 | C₃H₇ | —CH₂CH=CH₂ | 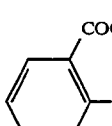 | 0 | 128 |
| 19 | C₃H₇ | C₃H₇ | 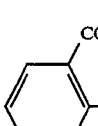 | 0 | 137 |
| 20 | C₃H₇ | CH(CH₃)₂ | 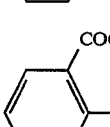 | 0 | 121 |
| 21 | CH₃ | C₂H₅ | 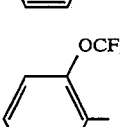 | 0 | 133 |
| 22 |  | —CH₂CH=CH₂ | 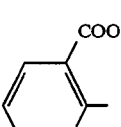 | 0 | 151 |
| 23 |  | C₃H₇ | 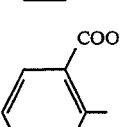 | 0 | 149 |
| 24 |  | CH(CH₃)₂ | 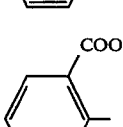 | 0 | 163 |
| 25 | C₃H₇ | CH₃ | 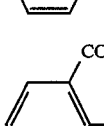 | 0 | 144 |

TABLE 3-continued

Preparation Examples of the compounds of the formula (I)

| Ex. No. | R¹ | R² | R³ | n | Melting point (°C.) |
|---|---|---|---|---|---|
| 26 | $C_3H_7$ | $C_2H_5$ | 2-(COOCH₃)-phenyl | 0 | 130 |
| 27 | cyclopropyl | $C_2H_5$ | 2-(COOCH₃)-phenyl | 0 | 173 |
| 28 | cyclopropyl | $CH_3$ | 2-(COOCH₃)-phenyl | 0 | 173 |
| 29 | —CH₂—CH=CH₂ | $CH_3$ | 2-(COOCH₃)-phenyl | 0 | 137 |
| 30 | —CH₂—CH=CH₂ | $C_2H_5$ | 2-(COOCH₃)-phenyl | 0 | 128 |
| 31 | cyclopropyl | $CH_3$ | 2-(OCF₃)-phenyl | 0 | 182 |
| 32 | cyclopropyl | $C_2H_5$ | 2-(OCF₃)-phenyl | 0 | 152 |
| 33 | $CH_3$ | $CH_3$ | 2-(COOCH₃)-phenyl | 2 | 176 |
| 34 | $CH_3$ | $C_2H_5$ | 2-Cl-3-CH₃-phenyl | 0 | 138 |
| 35 | $CH_3$ | $CH_3$ | 2-Cl-3-CH₃-phenyl | 0 | 175 |

TABLE 3-continued

Preparation Examples of the compounds of the formula (I)

| Ex. No. | R$^1$ | R$^2$ | R$^3$ | n | Melting point (°C.) |
|---|---|---|---|---|---|
| 36 | —CH$_2$—CH=CH$_2$ | —CH$_2$—CH=CH$_2$ | 2-(COOCH$_3$)phenyl | 0 | 101 |
| 37 | cyclopropyl | CH$_3$ | 2-Cl-3-CH$_3$-phenyl | 0 | 190 |
| 38 | cyclopropyl | C$_2$H$_5$ | 2-Cl-3-CH$_3$-phenyl | 0 | 163 |
| 39 | —CH$_2$—CH=CH$_2$ | CH$_3$ | 2-(OCF$_3$)phenyl | 0 | 163 |
| 40 | —CH$_2$—CH=CH$_2$ | C$_2$H$_5$ | 2-(OCF$_3$)phenyl | 0 | 133 |
| 41 | CH$_3$ | C$_3$H$_7$ | 2-(OCF$_3$)phenyl | 0 | 133 |
| 42 | C$_2$H$_5$ | —CH$_2$—CH=CH$_2$ | 2-(OCF$_3$)phenyl | 0 | 107 |
| 43 | cyclopropyl | C$_3$H$_7$ | 2-(OCF$_3$)phenyl | 0 | 121 |
| 44 | —CH$_2$—CH=CH$_2$ | C$_3$H$_7$ | 2-(COOCH$_3$)phenyl | 0 | 124 |
| 45 | —CH$_2$—CH=CH$_2$ | CH(CH$_3$)$_2$ | 2-(COOCH$_3$)phenyl | 0 | 94 |

TABLE 3-continued
Preparation Examples of the compounds of the formula (I)
| Ex. No. | R¹ | R² | R³ | n | Melting point (°C.) |
|---|---|---|---|---|---|
| 46 | CH₃ | CH(CH₃)₂ | 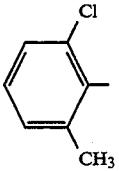 | 0 | 142 |
| 47 | —CH₂—CH=CH₂ | CH₃ | 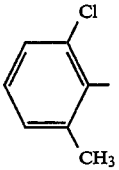 | 0 | 165 |
| 48 | —CH₂—CH=CH₂ | C₂H₅ | 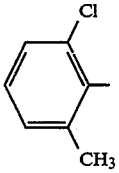 | 0 | 140 |
| 49 |  | CH(CH₃)₂ | 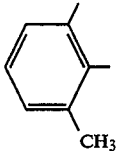 | 0 | 131 |
| 50 |  | C₃H₇ | 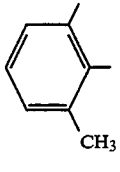 | 0 | 138 |
| 51 | C₂H₅ | CH₃ | 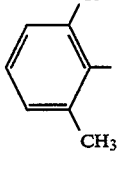 | 0 | 168 |
| 52 | C₂H₅ | C₂H₅ | 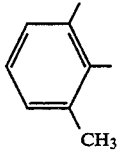 | 0 | 129 |
| 53 | CH₃ | C₃H₇ | 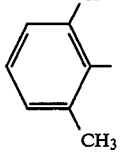 | 0 | 146 |

TABLE 3-continued

Preparation Examples of the compounds of the formula (I)

| Ex. No. | R¹ | R² | R³ | n | Melting point (°C.) |
|---|---|---|---|---|---|
| 54 | $CH_3$ | $-CH_2-CH=CH_2$ | 2-Cl-3-CH₃-phenyl | 0 | 125 |
| 55 | cyclopropyl | $-CH_2-CH=CH_2$ | 2-Cl-3-CH₃-phenyl | 0 | 141 |
| 56 | $C_2H_5$ | $C_3H_7$ | 2-Cl-3-CH₃-phenyl | 0 | 122 |
| 57 | $C_2H_5$ | $-CH_2-CH=CH_2$ | 2-Cl-3-CH₃-phenyl | 0 | 96 |
| 58 | $-CH_2-CH=CH_2$ | $-CH_2-CH=CH_2$ | 2-Cl-3-CH₃-phenyl | 0 | 113 |
| 59 | $-CH_2-CH=CH_2$ | $C_3H_7$ | 2-Cl-3-CH₃-phenyl | 0 | 102 |
| 60 | $-CH_2-CH=CH_2$ | $CH(CH_3)_2$ | 2-Cl-3-CH₃-phenyl | 0 | 122 |
| 61 | $CH_3$ | $CH(CH_3)_2$ | 2-OCF₃-phenyl | 0 | 106 |
| 62 | $CH_3$ | $-CH_2-CH=CH_2$ | 2-OCF₃-phenyl | 0 | 125 |

TABLE 3-continued

Preparation Examples of the compounds of the formula (I)

| Ex. No. | R¹ | R² | R³ | n | Melting point (°C.) |
|---|---|---|---|---|---|
| 63 |  | —CH₂—CH=CH₂ | 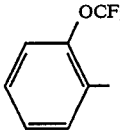 2-OCF₃-phenyl | 0 | 128 |
| 64 |  | CH(CH₃)₂ | 2-OCF₃-phenyl | 0 | 127 |
| 65 | C₂H₅ | CH₃ | 2-OCF₃-phenyl | 0 | 171 |
| 66 | C₂H₅ | C₂H₅ | 2-OCF₃-phenyl | 0 | 138 |
| 67 | —CH₂—CH=CH₂ | C₃H₇ | 2-OCF₃-phenyl | 0 | 89 |
| 68 | C₂H₅ | C₃H₇ | 2-OCF₃-phenyl | 0 | 127 |
| 69 | —CH₂—CH=CH₂ | CH(CH₃)₂ | 2-OCF₃-phenyl | 0 | 117 |
| 70 | —CH₂—CH=CH₂ | —CH₂—CH=CH₂ | 2-OCF₃-phenyl | 0 | 79 |
| 71 | C₂H₅ | CH(CH₃)₂ | 2-Cl-6-CH₃-phenyl | 0 | 137 |
| 72 | CH₃ | CH₃ | 3-methyl-2-(COOCH₃)-thienyl | 0 | 193–194 |
| 73 | CH₃ | C₂H₅ | 3-methyl-2-(COOCH₃)-thienyl | 0 | 176–177 |

TABLE 3-continued
Preparation Examples of the compounds of the formula (I)
| Ex. No. | R¹ | R² | R³ | n | Melting point (°C.) |
|---|---|---|---|---|---|
| 74 |  | CH₃ | 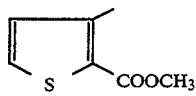 | 0 | 175–177 |
| 75 |  | C₂H₅ | 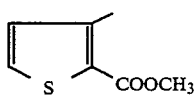 | 0 | 153–155 |
| 76 | N(CH₃)₂ | CH₃ | 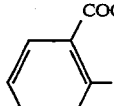 | 0 | 178–179 |
| 77 | N(CH₃)₂ | C₂H₅ | 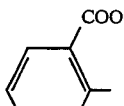 | 0 | 134–136 |
| 78 |  | CH₃ | 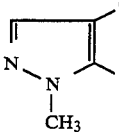 | 0 | 188–191 |
| 79 | CH₃ | CH₃ | 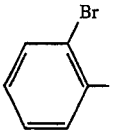 | 0 | 176–179 |
| 80 | CH₃ | C₂H₅ | 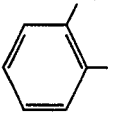 | 0 | 154–156 |
| 81 |  | CH₃ | 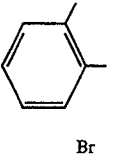 | 0 | 192–195 |
| 82 |  | C₂H₅ | 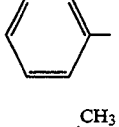 | 0 | 151–154 |
| 83 | CH₃ | CH₃ | 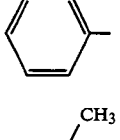 | 0 | 157 |
| 84 |  | CH₃ | 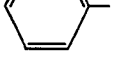 | 0 | 168 |

TABLE 3-continued

Preparation Examples of the compounds of the formula (I)

| Ex. No. | R¹ | R² | R³ | n | Melting point (°C.) |
|---|---|---|---|---|---|
| 85 | CH₃ | C₂H₅ | 2-CH₃-phenyl | 0 | 132 |
| 86 | cyclopropyl | C₂H₅ | 2-CH₃-phenyl | 0 | 137 |
| 87 | —CH₂—CH=CH₂ | —CH₂—C≡CH | 2-COOCH₃-phenyl | 0 | 95 |
| 88 | cyclopropyl | —CH₂—C≡CH | 2-COOCH₃-phenyl | 0 | 128–131 |
| 89 | CH₃ | —CH₂—C≡CH | 2-COOCH₃-phenyl | 0 | 143–144 |
| 90 | CH₃ | —CH(CH₃)₂ | 2-CH₃-phenyl | 0 | 107–109 |
| 91 | CH₃ | —CH(CH₃)₂ | 2-Br-phenyl | 0 | 103–104 |
| 92 | CH₃ | —CH(CH₃)₂ | 2-CF₃-phenyl | 0 | 114–117 |
| 93 | cyclopropyl | CH₃ | 2-CF₃-phenyl | 0 | 194–195 |
| 94 | cyclopropyl | C₂H₅ | 2-CF₃-phenyl | 0 | 150–152 |

TABLE 3-continued

| Ex. No. | R¹ | R² | R³ | n | Melting point (°C.) |
|---|---|---|---|---|---|
| 95 | CH₃ | C₂H₅ | 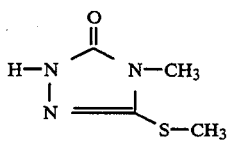 | 0 | 146–148 |

Starting substances of the formula (TI)

Example (II 1)

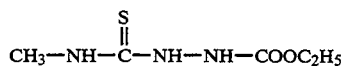

Step 1

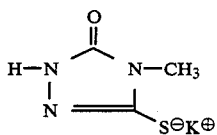

A solution of 175 g (2.4 mol) of methyl isothiocyanate in 300 ml of diethyl ether is added to a solution of 250 g (2.4 mol) of ethyl hydrazinoformate, with stirring. The reaction mixture is stirred for 12 hours at 20° C. and then cooled to about 10° C., and the product which is obtained in crystalline form is isolated by filtration with suction. This gives 404 g (95% of theory) of 4-methyl-1-ethoxycarbonylthiosemicarbazide of melting point 130° C.

The following are obtained analogously:
4-ethyl-1-methoxycarbonyl-thiosemicarbazide (melting point: 142° C.);
4-propyl-1-methoxycarbonyl-thiosemicarbazide (melting point: 117° C.
4-cyclopropyl-1-methoxycarbonyl-thiosemicarbazide (melting point: 148° C.);
4-allyl-1-methoxycarbonyl-thiosemicarbazide (melting point: 151° C.);
4-dimethylamino-1-methoxycarbonyl-thiosemicarbazide (melting point: 144° C.).

Step 2

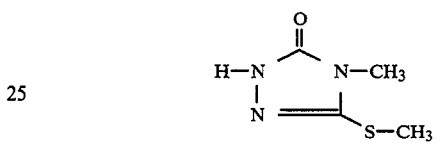

A mixture of 10.0 g (56.5 mmol) of 4-methyl-1-ethoxycarbonyl-thiosemicarbazide (cf. Step 1), 4.0 g (29 mmol) of potassium carbonate and 80 ml of ethanol is refluxed until the evolution of gas has ceased (about 3 hours). When the mixture is cold, it is concentrated, the residue is stirred with 50 ml of methylene chloride, and the product, which has remained undissolved, is isolated by filtration with suction.

This gives 9.2 g (96% of theory) of the potassium salt of 5-mercapto-4-methyl-2,4-dihydro-3H-1,2,4-triazol-3-one (melting point >230° C.).

The potassium salts of 5-mercapto-4-ethyl-2,4-dihydro-3H-1,2,4-triazol-3-one, 5-mercapto-4-propyl-2,4-dihydro-3H-1,2,4-triazol-3-one, 5-mercapto-4-cyclopropyl-2,4-dihydro-3H-1,2,4-triazol-3-one, and 5-mercapto-4-allyl-2,4-dihydro-3H-1,2,4-triazol-3-one, and 5-mercapto-4-dimethylamino-2,4-dihydro-3H-1,2,4-triazol-3-one, all of which melt above 230° C., are obtained analogously.

Step 3

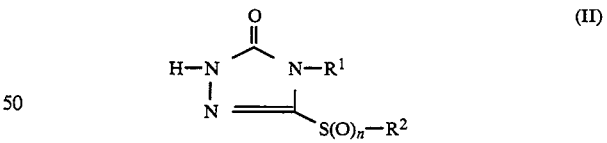

A mixture of 4.0 g (23.7 mmol) of the potassium salt of 5-mercapto-4-methyl-2,4-dihydro-3H-1,2,4-triazol-3-one (cf. Step 2), 4.1 g (28.9 mmol) of methyl iodide and 80 ml of methanol is stirred for 12 hours at 20° C. The mixture is then concentrated, the residue is stirred with methylene chloride, and the potassium iodide, which has remained undissolved, is separated off by filtration. The filtrate is concentrated, the residue is stirred with 500 ml of diethyl ether/petroleum ether (1:1 by vol.), and the product which has been obtained in crystalline from is isolated by filtration with suction.

This gives 3.4 g (99% of theory) of 4-methyl-5-methylthio-2,4-dihydro-3H-1,2,4-triazol-3-one of melting point 97° C.

For example the compounds of the formula (II) listed in Table 4 below can also be prepared analogously to Example (II-1).

$$\text{H—N} \overset{\overset{\text{O}}{\|}}{\underset{|}{\text{C}}} \text{N—R}^1 \\ \text{N} = \text{S(O)}_n\text{—R}^2 \tag{II}$$

TABLE 4

| Preparation Examples of the compounds of the formula (II) | | | | |
|---|---|---|---|---|
| Ex. No. | R¹ | R² | n | m.p. (°C.) (Refractive index) |
| II-2 | CH₃ | C₂H₅ | 0 | 97 |
| II-3 | CH₃ | C₃H₇ | 0 | 50 |
| II-4 | CH₃ | CH(CH₃)₂ | 0 | 91 |
| II-5 | CH₃ | —CH₂CH=CH₂ | 0 | 58 |
| II-6 | CH₃ | —CH₂C₆H₅ | 0 | |
| II-7 | C₂H₅ | CH₃ | 0 | 95 |
| II-8 | C₂H₅ | C₂H₅ | 0 | 87 |
| II-9 | C₂H₅ | C₃H₇ | 0 | 73 |
| II-10 | C₂H₅ | CH(CH₃)₂ | 0 | 42 |
| II-11 | C₂H₅ | —CH₂CH=CH₂ | 0 | (n$_D^{20}$: 1,5400) |
| II-12 | C₂H₅ | —CH₂C₆H₅ | 0 | |
| II-13 | C₃H₇ | CH₃ | 0 | 78 |
| II-14 | C₃H₇ | C₂H₅ | 0 | (n$_D^{20}$: |

TABLE 4-continued

Preparation Examples of the compounds of the formula (II)

| Ex. No. | R¹ | R² | n | m.p. (°C.) (Refractive index) |
|---|---|---|---|---|
| II-15 | C₃H₇ | C₃H₇ | 0 | 56 |
| II-16 | C₃H₇ | CH(CH₃)₂ | 0 | 55 |
| II-17 | C₃H₇ | —CH₂CH=CH₂ | 0 | ($n_D^{20}$: 1.5350) |
| II-18 | CH(CH₃)₂ | CH₃ | 0 | 1,5215) |
| II-19 |  | CH₃ | 0 | 160 |
| II-20 | 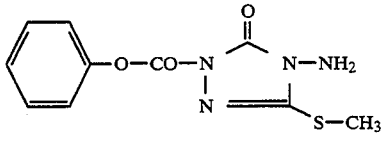 | C₂H₅ | 0 | 119 |
| II-21 | 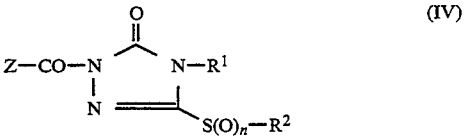 | C₃H₇ | 0 | 94 |
| II-22 | 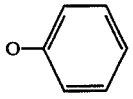 | CH(CH₃)₂ | 0 | 94 |
| II-23 | 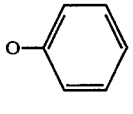 | —CH₂CH=CH₂ | 0 | 105 |
| II-24 | —CH₂C₆H₅ | CH₃ | 0 | 135 |
| II-25 | —CH₂CH=CH₂ | CH₃ | 0 | 70 |
| II-26 | —CH₂CH=CH₂ | C₂H₅ | 0 | 55 |
| II-27 | CH₃ | CH₃ | 2 | 166 |
| II-28 | —CH₂—CH=CH₂ | —CH₂—CH=CH₂ | 0 | (amorphous)* |
| II-29 | —CH₂—CH=CH₂ | CH(CH₃)₂ | 0 | 57 |
| II-30 | —CH₂—CH=CH₂ | C₃H₇ | 0 | 45 |
| II-31 | —N(CH₃)₂ | CH₃ | 0 | 168–169 |
| II-32 | —N(CH₃)₂ | C₂H₅ | 0 | 146 |
| II-33 | CH₃ | —CH₂—C≡CH | 0 | 153 |
| II-34 | 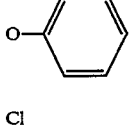 | —CH₂—C≡CH | 0 | 153–154 |
| II-35 | —CH₂—CH=CH₂ | —CH₂—C≡CH | 0 | 102–103 |

*¹H-NMR (D₆-DMSO, 360 MHz): δ = 3,66(d, S—C$\underline{H}_2$—); 4,17(m, N—C$\underline{H}_2$—); 4,95–5,28(m, 2C$\underline{H}_2$=); 5,75–5,99(m, 2C$\underline{H}$=); 12,0(N$\underline{H}$) ppm.

Starting substances of the formula (IV):

Example (IV-1)

$$\text{C}_6\text{H}_5\text{—O—CO—N}\begin{array}{c}\text{O}\\\|\\\text{C}\end{array}\text{N—NH}_2$$
with ring containing N, N and =C—S—CH₃

22.1 g (0.141 mol) of phenyl chloroformate are added to a mixture of 20.0 g (0.137 mol) of 4-amino-5-methylthio-2,4-dihydro-3H-1,2,4-triazol-3-one, 5.6 g (0.141 mol) of sodium hydroxide, 0.2 g of tetrabutylammonium bromide and 200 ml of methylene chloride/water (1:1, by vol.), with vigorous stirring. The reaction mixture is stirred for 12 hours at 20° C., and the product which is obtained in crystalline form is isolated by filtration with suction. This gives 34.8 g (95% of theory) of 4-amino-5-methylthio-2-phenoxycarbonyl-2,4-dihydro-3H-1,2,4-triazol-3-one of melting point 211° C.

For example the compounds of the formula (IV) listed in Table 5 below can also be prepared analogously to Example (IV-1).

$$\text{Z—CO—N}\begin{array}{c}\text{O}\\\|\\\text{C}\end{array}\text{N—R}^1 \quad \text{(IV)}$$
with N—N=C—S(O)ₙ—R²

TABLE 5

Preparation Examples of the compounds of the formula (IV)

| Ex. No. | R¹ | R² | n | Z | Melting point (°C.) |
|---|---|---|---|---|---|
| IV-2 | CH₃ | CH₃ | 0 | —O—C₆H₅ | 166 |
| IV-3 | CH₃ | C₂H₅ | 0 | —O—C₆H₅ | 112 |
| IV-4 | C₂H₅ | C₂H₅ | 0 | —O—C₆H₅ | |
| IV-5 | CH₃ | C₃H₇ | 0 | Cl | |

TABLE 5-continued
Preparation Examples of the compounds of the formula (IV)
| Ex. No. | R¹ | R² | n | Z | Melting point (°C.) |
|---|---|---|---|---|---|
| IV-6 | CH₃ | CH₂—CH=CH₂ | 0 | 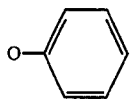 | |
| IV-7 |  | CH₃ | 0 | 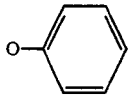 | 143 |
| IV-8 |  | C₂H₅ | 0 | 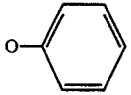 | 84 |
| IV-9 |  | C₃H₇ | 0 | 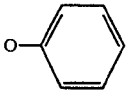 | |
| IV-10 |  | CH₂—CH=CH₂ | 0 | 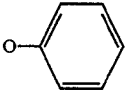 | |
| IV-11 | OCH₃ | CH₃ | 0 | 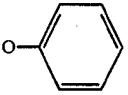 | |
| IV-12 | OC₂H₅ | C₂H₅ | 0 | 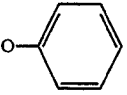 | |
| IV-13 | OCH₂—CH=CH₂ | C₂H₅ | 0 | 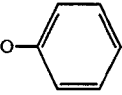 | |
| IV-14 |  | CH(CH₃)₂ | 0 | Cl | |
| IV-15 | C₂H₅ | CH₃ | 0 | Cl | |
| IV-16 | C₂H₅ | C₃H₇ | 0 | 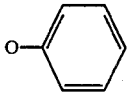 | |
| IV-17 | NH—CH₃ | CH₃ | 0 | 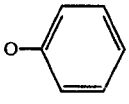 | |
| IV-18 | NH—CH₃ | C₂H₅ | 0 | 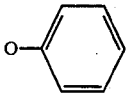 | |
| IV-19 | N(CH₃)₂ | C₂H₅ | 0 | 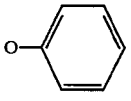 | |

TABLE 5-continued
Preparation Examples of the compounds of the formula (IV)

| Ex. No. | R¹ | R² | n | Z | Melting point (°C.) |
|---------|----|----|---|---|---------------------|
| IV-20 | NH—CH$_3$ | C$_3$H$_7$ | 0 | —O—C$_6$H$_5$ | |
| IV-21 | NH—CH$_3$ | CH(CH$_3$)$_2$ | 0 | —O—C$_6$H$_5$ | |
| IV-22 | NH—CH$_3$ | CH$_2$—CH=CH$_2$ | 0 | —O—C$_6$H$_5$ | |
| IV-23 | CH$_2$—CH=CH$_2$ | C$_2$H$_5$ | 0 | —O—C$_6$H$_5$ | |

Use Examples

In the Use Examples which follow, the known herbicide isocarbamid, of the formula (A) below, is used as comparison substance:

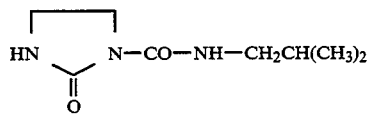
(A)

(disclosed in, for example, DE-1,795,117).

In the text below, the formulae of the compounds according to the invention used for the Use Examples are listed individually, the numbers being those of the Preparation Examples:

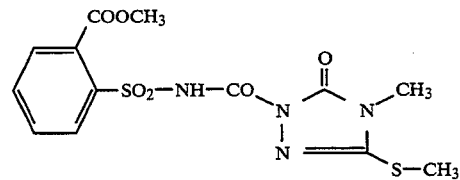
(1)

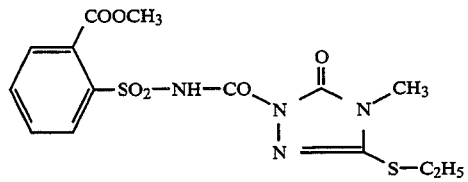
(3)

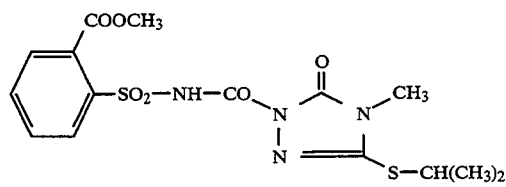
(4)

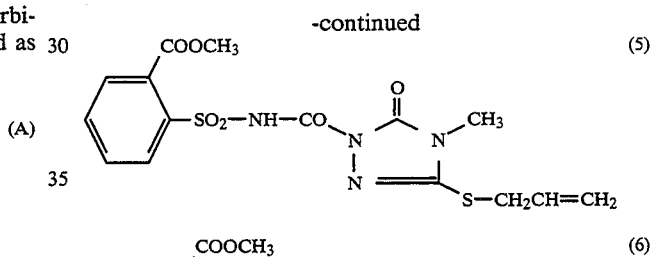
(5)

(6)

(7)

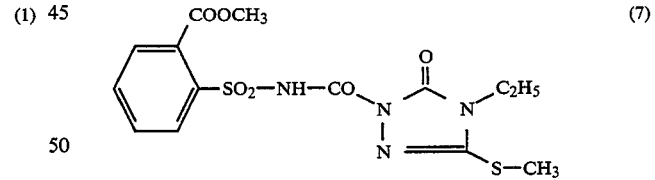
(9)

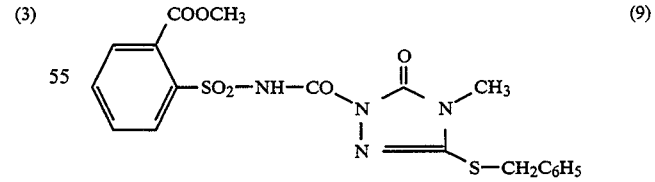

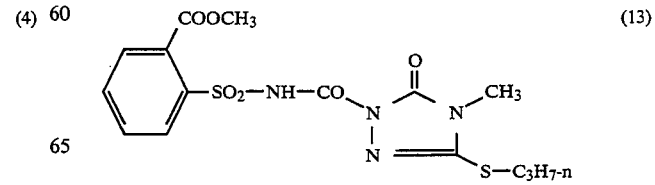
(13)

-continued
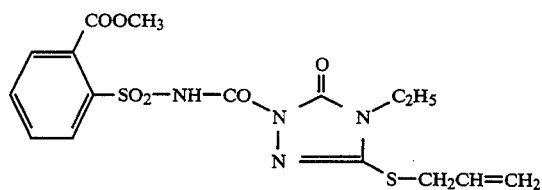 (14)
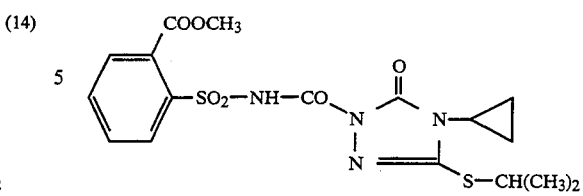 (24)
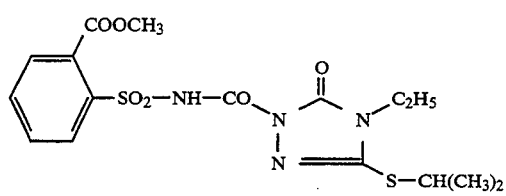 (15)
 (25)
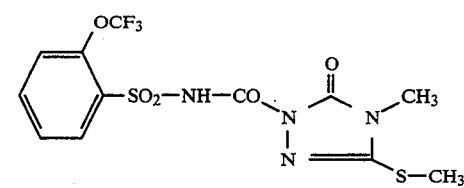 (16)
 (26)
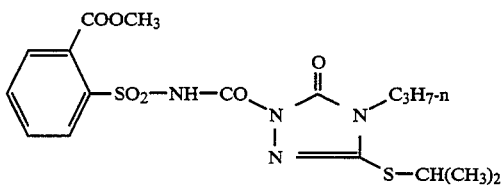 (17)
 (27)
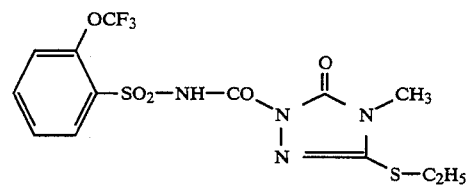 (20)
 (28)
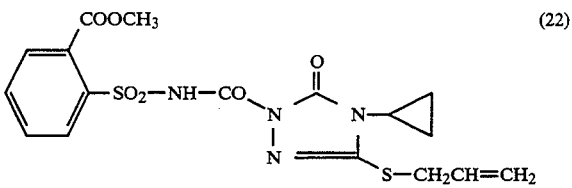 (21)
 (29)
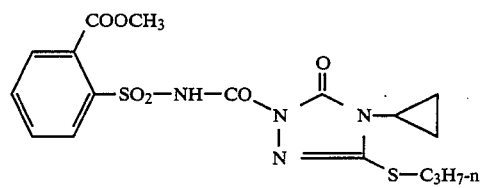 (22)
(30)
(23)
(31)

-continued

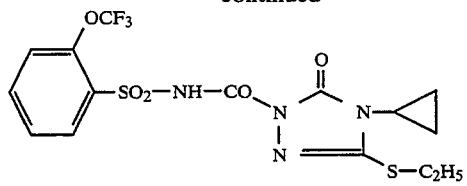 (32)

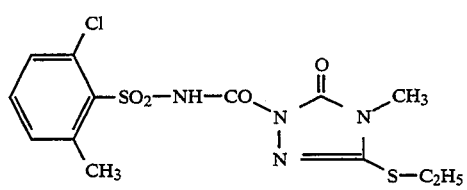 (34)

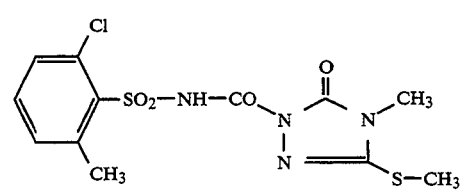 (35)

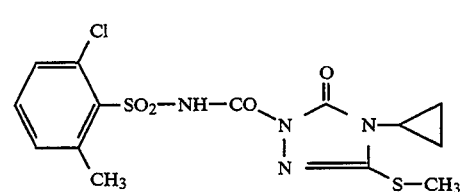 (37)

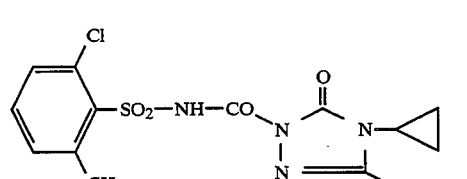 (38)

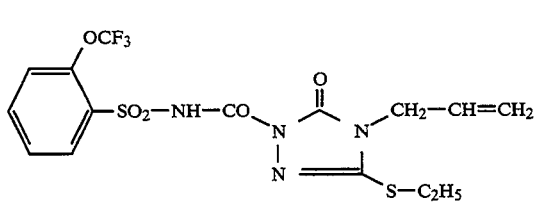 (40)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount emulsifier is added and the concentrate is diluted with water to the desired concentration.

Seeds of the test plants are sown in normal soil and, after 24 hours, watered with the preparation of the active compound. It is expedient to keep the amount of water per unit area constant. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds of Preparation Examples: 1, 3, 4, 5, 6, 7, 13, 17, 21, 22, 23, 24, 25, 26, 27, 28, 29, 30, 31, 32, 34, 35, 37.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds of Preparation Examples: 1, 3, 4, 5, 6, 7, 13, 14, 16, 17, 20, 21, 22, 23, 24, 25, 26, 27, 28, 29, 30, 31, 32, 34, 35, 37, 38, 40.

Example C

Pyricularia test (rice)/protective
Solvent: 12,5 parts by weight of acetone
Emulsifier: 0,3 parts by weight of alkylarylpolyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia orycae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 1, 3, 4, 5, 7, 9.

Example D

Pyricularia test (rice)/systemic
Solvent: 12,5 parts by weight of acetone
Emulsifier: 0,3 parts by weight of alkylarylpolyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° and a relative atmospheric humidity of 100% until they are evaluated. Evaluation of the disease infestation is carried out 4 days after the inocualtion.

In this test, a clearly superior activity compared with the prior art is shown, for example, by the compounds according to the following preparation examples: 1, 3, 4, 5, 7, 15, 17, 21, 22, 25.

It will be appreciated that the instant specification and claims are set forth by way of illustration and not limitation, and that various modifications and changes may be made without departing from the spirit and scope of the present invention.

We claim:

1. A triazolinone of the formula $$\text{(II)}$$

in which
    n represents the numbers 0, 1, or 2,
    $R^1$ represents di-($C_1$-$C_4$-alkyl)-amino, and
    $R^2$ represents $C_1$-$C_6$-alkyl.

2. The compound of the Formula (II) according to claim 1, in which
    n represents the number 0,
    $R^1$ represents dimethylamino, and
    $R^2$ represents methyl.

3. The compound of the Formula (II) according to claim 1, in which
    represents the number 0,
    $R^1$ represents dimethylamino, and
    $R^2$ represents ethyl.

* * * * *

UNITED STATES PATENT AND TRADEMARK OFFICE
CERTIFICATE OF CORRECTION

PATENT NO. : 5,380,863
DATED : January 10, 1995
INVENTOR(S) : Muller, et al.

It is certified that error appears in the above-identified patent and that said Letters Patent is hereby corrected as shown below:

Col. 62, claim 3  Before " represents " insert -- n --
line 3

Signed and Sealed this

Eleventh Day of August 1998

Attest:

BRUCE LEHMAN

Attesting Officer         Commissioner of Patents and Trademarks